United States Patent [19]

Koga et al.

[11] Patent Number: 5,283,239
[45] Date of Patent: Feb. 1, 1994

[54] INHIBITOR OF HERPESVIRUS ABSORPTION

[75] Inventors: Junichi Koga, Kobe; Yasuhiro Ohashi, Noda; Hajime Hiratani, Sennan, all of Japan

[73] Assignees: JCR Pharmaceuticals Co. Ltd., Hyogo; Noda Shokukin Kogyo Co., Ltd., Chiba, both of Japan

[21] Appl. No.: 823,061

[22] Filed: Jan. 14, 1992

Related U.S. Application Data

[63] Continuation of Ser. No. 473,447, Feb. 1, 1990, abandoned.

[30] Foreign Application Priority Data

Feb. 10, 1989 [JP] Japan .................................. 1-32058

[51] Int. Cl.$^5$ ............................................. A61K 31/70
[52] U.S. Cl. ...................... 514/23; 514/934; 424/195.1
[58] Field of Search ................ 424/195.1; 514/934, 514/23

[56] References Cited

U.S. PATENT DOCUMENTS

| | | | |
|---|---|---|---|
| 4,461,760 | 7/1984 | Sugano et al. | 424/195.1 |
| 4,629,627 | 12/1986 | Iizuka | 424/195.1 |

FOREIGN PATENT DOCUMENTS

| | | | |
|---|---|---|---|
| 1220136 | 7/1987 | Canada | 424/195.1 |

*Primary Examiner*—John W. Rollins
*Attorney, Agent, or Firm*—Burgess, Ryan & Wayne

[57] ABSTRACT

LEM which is an aqueous extract of a mycelial culture of *Lentinus Edodes* and has a sugar composition composed of arabinose, xylose, glucose, mannose, galasctose, fucose and rhamnose, as well as a fraction of LEM which corresponds to molecular weights of 10,000 to 1,000,000 daltons and has a sugar composition composed of arabinose, xylose, glucose, mannose and galactose are provided as agents for inhibiting the adsorption of herpesviruses such as herpes simplex to the cells.

12 Claims, 1 Drawing Sheet

INHIBITOR OF HERPESVIRUS ABSORPTION

This application is a continuation of application Ser. No. 473,447, filed Feb. 1, 1990, now abandoned.

BACKGROUND OF THE INVENTION

1) Field of the Invention

This invention relates to inhibitory agents against adsorption of herpesviruses to cells.

2) Description of the Related Art

It is well known that herpesviruses come to act as causative agents for various diseases. As an example of herpesviruses, there may be mentioned herpes simplex virus, which is one of the most typical represetantive of the family *Herptoviridae* consisting of *varicella herpse zoster*, cytomegalovirus, EB virus, etc. Herpes simplex virus contains double-stranded DNA with a molecular weight of 85 to $100 \times 10^6$ daltons which is enclosed in a regular been known to have on its envelope six to eight species of glycoproteins with different antigenicities (Longnecker et al.; Proc. Natl. Acad. Sci. USA 84, 4302 (1987)).

This virus can be further classified into two subtypes, herpes simplex virus type 1 and type 2, which are considered to cause mainly stomatitis and genital herpes, respectively, but there is no strict distinction between these two subtypes. The typical diseases, for which this virus is regarded to be responsible, include not only the two diseases as described above but also a wide variety of diseases, such as keratitis, menigism, upper and lower respiratory tract infections and facial palsy. The virus, after initial infection, causes hosts to acquire inapparent infection, thereby making almost all human adults positive to its antibody. However, the antibody negativity ratio in adults has risen recently, and it is clarified that the initial infection of herpes simplex virus in expectant and nursing mothers causes extremely severe diseases in fetuses.

Development of various antiviral agents being directed toward this virus has heretofore been under progress, but a very few drug substances have been clinically confirmed so far for efficacy; only adenine arabinoside and aciclovir are clinically effective.

In recent years, anti-tumor factors contained in some components of *Lentinus edodes* have been in clinical use. Such anti-tumor factors, as exemplified by Krestin (Yanagawa et al.; "*Gan to Kagakuryohou* (Cancer and Chemotherapy), 11, 2155 (1985)) and Lentinan (Suga et al.; Cancer Research, 44, 5162 (1984)), are considered to owe their pharmacological activities to glycoproteins polysaccharide components contained therein. In addition, polysaccharides having sulfuric acid radicals such as dextran sulfate sodium were reported to exhibit activities against AIDS virus (Mitsuya et al., "Science", 248, 646 (1988)).

Furthermore, an aqueous extract of mycelial cultures of *Lentinus edodes* is called briefly "LEM", and a process for the production of the same is described in Japanese Patent Publication No. Sho 53-10117. LEM has been utilized as an agrochemical effective for the suppression of tobacco mosaic virus, and its therapeutic effect for hepatitis is also suggested (Harada et al.; "Kan-Tan-Sui, 14, No. 2, 327: Sugano et al.; "Cancer Letters", 17, 109 (1982); Suzuki et al.; *Igaku no Ayumi* (Progress on Medicine) 138 441 (1986)). LEM, when assayed with RNA of tobacco mosaic virus as a substrate, was confirmed to exhibit inhibition of the activity of reverse transcriptase derived from bird myeloma virus. This drug substance, when analyzed for its sugar compositon, was found to be specifically characterized by an extremely high content each of arabinose and xylose, indicating that the substance is clearly in contrast with Krestin and Lentinan which both have a sugar composition constituted almost exclusively of glucose.

Aciclovir as mentioned in the above, though it is considered to produce enhanced efficacy, shows a high degree of toxicity just as is the case with other nucleic acid antagonists. Under these circumstances, there is a strong demand for a safer and more effective medicine that can demonstrate therapeutic effect through different mechanism of action.

In addition, there has not yet been any satisfactory medicine available so far, that is capable of effectively inhibiting infection with the family *Herpetoviridae* inclusive of herpes simplex virus, without producing serious side effects to human body. This invention is intended to provide, from an entirely novel point of view, a medicine with a remarkably lowered degree of toxicity, which is quite different from nucleic acid analogs, in order to inhibit the adsorption of herpesviruses to cells and to block the proliferation of such viruses.

SUMMARY OF THE INVENTION

The present inventors, after continued research on LEM, found that this substance surprisingly possesses an exceedingly strong adsorption inhibitory activity against herpes simplex virus. Namely, the present inventors reacted LEM solutions of different concentrations with dilutions of various viruses at 37° C. for 1 to 3 hours and then contacted with animal cells sensitive to these individual viruses. After washing out of the virus dilutions, the presence and number of plaque formations on tissues were observed for 1 to 14 days. LEM showed extremely strong inhibition of plaque formation by herpesviruses, among other viruses. For example, the substance at concentrations of 5 to 10 ug/ml exhibited 50% inhibition against herpes simplex virus on monkey kidney Vero cells, whereas such activity was not detected at all in Krestin and Lentinan. By using this procedure as a guidance, the present inventors developed the fractionation and purification of LEM; an aqueous solution of this substance was neutralized and then subjected to precipitation with an organic solvent, such as methanol and ethanol, and the resultant precipitate was dissolved in water or a buffer, for example phosphate buffer, followed by fractionation with use of ion exchange chromatography and hydrophobic chromatography. The individual fractions thus obtained were further fractionated by use of gel permeation chromatography, with the result that a fraction which exists in electrically neutral range (pH 5 to 8.5) and has a molecular weight corresponding to 10,000 to 1,000,000 daltons was proven to demonstrate strong activity.

From the facts that this fraction, after having its protein removed, showed attenuated activity and that its activity correlated with its molecular weight distribution, protein distribution and sugar distribution, furthermore, it was suggested that the active factor could be composed essentially of a glycoprotein or proteoglycan. Some of the fractions thus obtained, at the concentration of 1 ug/ml demonstrated 50% inhibition against herpes simplex virus (HSV) type 1, while showing similar activity against HSV type 2. Dextran sulfate sodium, when assayed in this system, also exhibited the same inhibitory activity but required the minimum concentration of 5 ug/ml to achieve 50% inhibition against HSV type 1, with higher concentration being needed for 50% inhibition against HSV type 2. LEM, when its acute toxicity through oral administration was determined in rats and mice, showed a $LD_{50}$ value of 15 g/kg, being proven to be extremely low in toxicity. In the subacute toxicity test, the substance produced no dose-dependent change, except some animals were observed to develop loose feces which was assumed to be caused by dyspepsia.

This invention is based on the above described finding, and is concerned with a treatment agent for diseases caused by herpesviruses or an inhibitory agent against adsorption of such herpesviruses which contains an aqueous extract of a mycelial culture of *Lentinus edodes* or its fraction having a molecular weight corresponding to 10,000 to 1,000,000 daltons.

DESCRIPTION OF THE PREFERRED EMBODIMENTS

Cultivation of mycelia of *Lentinus edodes* has been carried out widely for the purpose of collecting fruit bodies, but in practicing this invention, it is preferred to extract the resultant mycelial culture with warm water in the stage just prior to the formation of fruit bodies. As the aqueous extract in this invention, there may be used an extract (LEM, on the market) obtainable by conducting the cultivation and extraction in accordance with the procedure as described in the Japanese Patent Publication Sho 53-10117 (1978), whereupon a strain of *Lentinus edodes* is cultured in a culture medium composed of bagasse and defatted rice bran. The fraction having a molecular weight corresponding to 10,000 to 1,000,000 in the aqueous extract can be produced by subjecting the aqueous extract to gel permeation chromatography.

The aqueous extract or purified fraction as described in the above can be administered parenterally or orally in order to inhibit the adsorption of herpesviruses to cells.

In order to treat skin symptoms brought about by the attack of herpesviruses or to inhibit the adsorption of the viruses, the aqueous extract or its fraction according to this invention can desirably be used in the form of preparations for external use being suited for local application to the skin, mucosa, etc. attacked or possibly attacked by the viruses. Locations of such skin and mucosa include openings of human body, such as the oral cavity, throat, nostil, eyelids, anus, rectum, urethra and vagina as well as injured portions and surroundings thereof.

The treatment or therapeutic agent or inhibitor of viral adsorption according to this invention, as processed in the form of preparations for external use, can be administered to a subject in such dosage forms as suppository, jelly, cream, cataplasma, ointment, plaster, injection, liquids, spray, aersol and powder for external use, as the case may be. Such preparations for external use can be prepared by the procedures known per se.

In order to prevent decomposition of the active ingredient with water during storage, for example, the aqueous extract or its fraction is desirably freeze-dried, followed by addition of water to the lyophilizate on the occasion of use.

The aqueous extract or its fraction of this invention may be administered orally in the dosage forms, such as powder, granule, pill and tablet, if desired. Such pharmaceutical preparations can be produced by the conventional methods.

In addition, the purified fraction can also be utilized for injection in the form of aqueous solution.

The aqueous extract or its purified fraction of this invention is preferably used in the proportions of about 1 to 5% as LEM in such preparations for external use, while it is desirably employed at the single dose of 10 to 10,000 mg for oral administration. The purified fraction can be used in quantities as reduced to one by several of those of LEM.

For the purpose of injection, the purified fraction can be utilized at the single dose in the range of 1 to 1,000 mg. Injectable solutions are desirably administered by subcutaneous injection.

In the present invention, the pharmaceutical preparations containing the aqueous extract of mycelial culture of *Lentinus edodes* or its fraction act to inhibit the bonding of herpesviruses to target cells to thereby block the infection with said viruses, onset of diseases caused by the viruses or spread of the affected lesions.

According to this invention, there can be provided the medicaments with an enhanced degree of safety being capable of inhibiting the adsorption of herpesviruses to cells.

DESCRIPTION OF THE DRAWING

Referring to the drawing.

Figure 1:
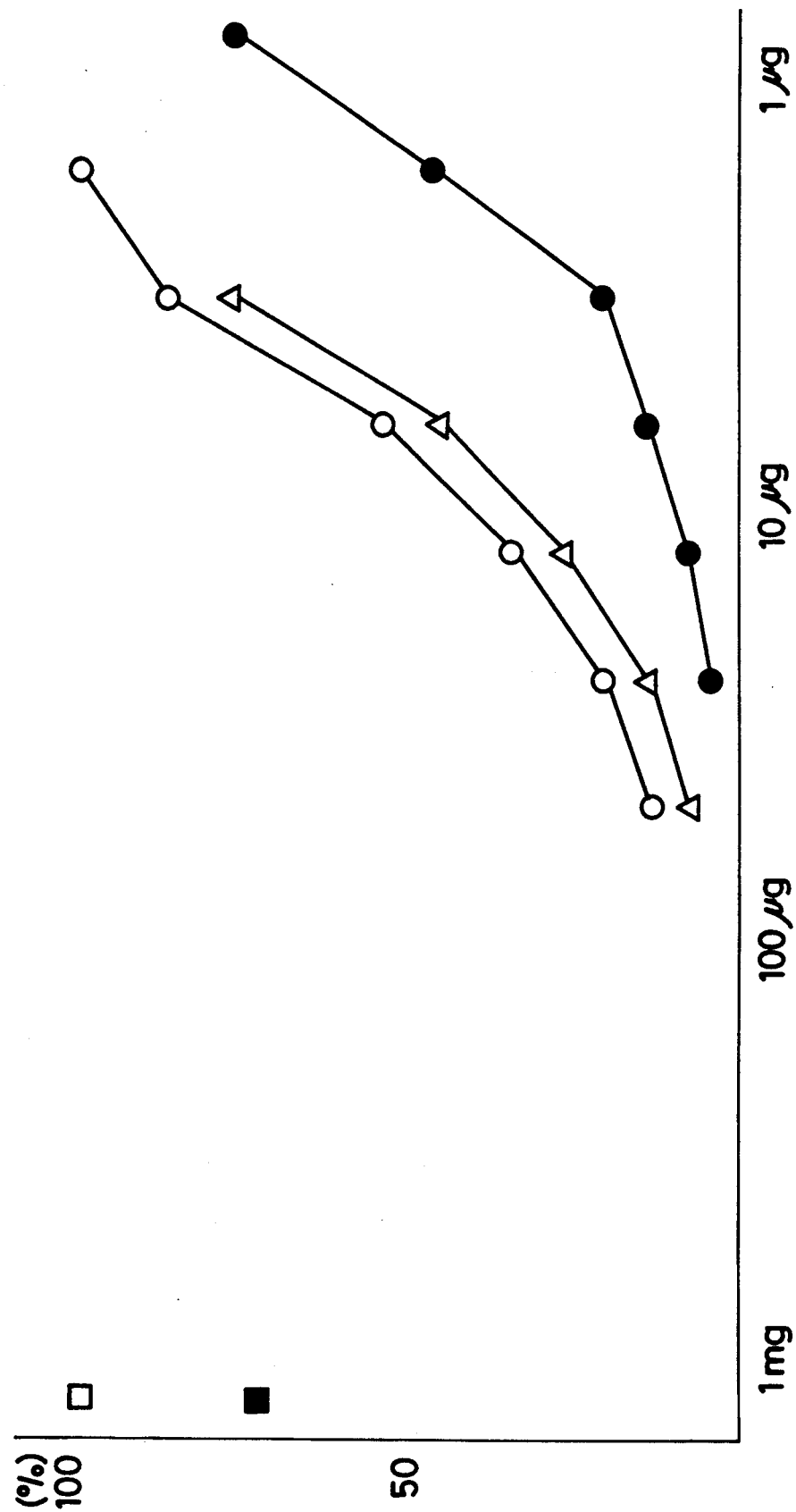
FIG. 1 is a summarized representation of adsorption-inhibitory activities as assayed in Example 3, where the percentages of numbers of plaques from cells treated with diluted solutions of individual test samples divided by numbers of plaques from non-treated cells are plotted on ordinate and concentrations of test samples on abscissa; the symbols, □, ■, △, ○ and ● designate Lentinan, Krestin, dextran sulfate sodium, LEM and Fraction 4, respectively.

LEM, which was used in the examples described below, is prepared and marketed by Noda Shokukin Kogyo K.K. located at Noda city, Chiba, Japan, and shows physico-chemical properties and the like as given in the following:

| Name: Extract of mycelial culture of *Lentinus edodes* (LEM) | |
| --- | --- |
| Constituents: | |
| Sugar; | 30 to 38% |
| Protein; | 10 to 12% |
| Ash; | 16 to 18% |
| Water; | 6 to 8% |
| Sugar composition: | |
| Arabinose; | 35.6 to 39.0% |
| Xylose; | 28.8 to 30.8% |
| Glucose; | 16.3 to 20.0% |
| Mannose; | 7.6 to 8.4% |
| Galactose; | 4.9 to 6.3% |
| Fucose + muranose; | 0.3 to 1.7% |
| Appearance: | |
| Brownish to dark brown granule or powder, bitter tasted. | |
| Solubilities: | |
| The substance is very slightly soluble in water and almost insoluble in ethanol and ether. | |
| Hygroscopicity: | |
| The substance is hygroscopic. | |

EXAMPLE 1

With a specific view to investigation into typical physical properties of the active factor contained in LEM, purification was carried out. 120 g of LEM was dissolved in 1 liter of distilled water, and after insoluble matter was removed by centrifugation, the supernatant liquid was fractionated by means of hydrophobic chromatography on Phenyl Sepharose (Pharmacia Co., Sweden) and gel permeation chromatography on Sephacryl S-300 (Pharmacia Co., Sweden).

The fractionation procedure is shown in the scheme of Table 1, while the sugar compositions of the resultant fractions are tabulated in Table 2.

TABLE 1

Fractionation of LEM

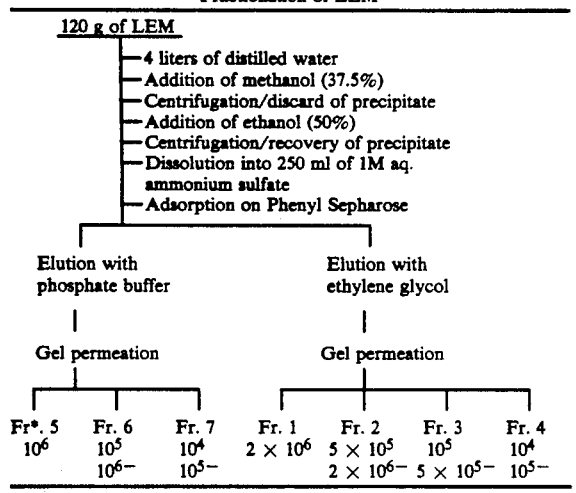

Note, *stands for fraction. Figures designate molecular weight ranges

TABLE 2

| | Sugar composition of each fraction | | | | |
|---|---|---|---|---|---|
| | Glucose (%) | Xylose (%) | Galactose (%) | Arabinose (%) | Mannose (%) |
| Fraction 1 | 77.9 | 12.6 | 4.2 | 5.3 | — |
| Fraction 2 | 30.3 | 45.7 | 5.7 | 18.3 | — |
| Fraction 3 | 30.9 | 48.1 | 4.3 | 16.7 | — |
| Fraction 4 | 25.5 | 48.5 | 5.6 | 17.3 | 3.1 |
| Fraction 5 | 81.0 | 8.0 | 2.7 | 6.0 | 2.3 |
| Fraction 6 | 65.2 | 2.3 | — | 32.2 | 5.2 |
| Fraction 7 | 49.3 | 43.7 | 7.0 | — | — |
| Krestin | 72.2 | 4.0 | 4.5 | — | 19.3 |
| Lentinan | 72.6 | — | 5.9 | 12.2 | 9.3 |

EXAMPLE 2

LEM was assayed for inhibitory activity against adsorption of viruses. Monkey kidney Vero cells were grown on a 24-holes plate (Nunc Co., Denmark) for tissue cultivation. Strain F of herpes simplex virus (distributed by Prof. R. J. Whitley of Clinical Virology Lab., University of Alabama) was diluted with a culture medium composed of Eagle MEM (Nissui Pharmaceuticals Co, Japan) containing 1% of serum (Dai-Nippon Pharmaceuticals Co., Japan) in such a manner as it contains 50 to 100 plaque forming units in 0.1 ml. Stepwise diluted solutions of LEM or its fraction and stepwise diluted solutions of a control drug were mixed with the diluted solution of the virus in equal portions, individually, to undergo reaction at 37° C. for 1 to 2 hours.

After washing cells in the plate with phosphate:buffer isotonic saline of Dulbecco's formulation (PBS, Nissui Pharm. Co., Japan), 0.1 ml portions of the reaction solution were poured into individual holes and contacted with cells for 1 hour. The cells were washed with PBS and overlaid for solidification with the above-mentioned culture medium containing 0.2% of agar, followed by cultivation in a $CO_2$ incubator for 2 days. In counting a number of plaques, the cells in individual holes were fixed with each 1 ml of 10% formalin (Wako Pure Chemicals Co., Japan) and dyed with each 0.5 ml of 0.03% Methylene Blue (Sigma Co., U.S.A.).

The results are shown in FIG. 1, where the percentages of numbers of plaques from the cells treated with each diluted solution of LEM divided by the ones from the cells not treated with LEM is plotted as ordinate and the concentrations of test samples as abscissa. In this figure. The symbols, □, ■, △, ○, and ● designate Lentinan, Krestin, dextran sulfate sodium, LEM and Fraction 4, respectively. The results indicate that LEM at the concentration of 5 ug/ml and Fraction 4 at 1 ug/ml (the concentrations as converted to sugar one) are capable of 50% inhibiting the plaque formation on the treated cells against the control. Fraction 4 exhibited inhibitory activity 500-fold or more as potent as Krestin and Lentinan as assayed together, while it developed the activity at lowered concentrations as compared with dextran sulfate sodium.

EXAMPLE 3

Dissolved in 0.025M phosphate buffer (pH 6.8) containing 0.9% (W/V) of sodium chloride was 5,000 ml (50 ug/ml) of Fraction 4 as obtained in Example 1, and the solution was sterile-filtered by use of Millipore filter and distributed in 2 ml portions into ampoules, followed by lyophilization to produce preparations for injection.

EXAMPLE 4

LEM powder was divided in 5 g quantities and wrapped to give preparations for oral administration.

EXAMPLE 5

In 10 ml of isotonic saline was dissolved 1 g of Fraction 4, and hyrophilic ointment was added little by little to the solution, while kneading, to produce 100 g of ointment in whole amount.

We claim:

1. An inhibitor against the adsorption of herpes simplex to cells, consisting essentially of a fraction of LEM which is an aqueous extract of a mycelial culture of *Lentinus Edodes* and has a sugar composition composed of arabinose, xylose, glucose, mannose, galactose, fucose and rhamnose, said fraction having a molecular weight of 10,000 to 100,000 daltons and having a sugar composition composed of arabinose, xylose, glucose, mannose and galactose.

2. An inhibitor against the adsorption of herpes simplex to cells according to claim 1, wherein the aqueous extract of a mycelial culture of *Lentinus Edodes* is an extract obtained by cultivating a strain of *Lentinus Edodes* in a culture medium composed of bagasse being admixed with rice bran, followed by extracting the resultant culture, prior to the formation of fruit bodies, with warm water.

3. A pharmaceutical composition useful for inhibiting the adsorption of herpes simplex to cells, said composition comprised of a therapeutically acceptable amount of the inhibitor of claim 2 and a pharmaceutically acceptable carrier.

4. A pharmaceutical composition useful for inhibiting the adsorption of herpes simplex to cells, said composition comprised of a therapeutically acceptable amount of the inhibitor of claim 1 and pharmaceutically acceptable carrier.

5. A method for inhibiting absorption of herpes simplex to cells which comprises applying to the cells an effective amount of a fraction of LEM which is an aqueous extract of a mycelial of *Lentinus Edodes* having a sugar composition comprised of arabinose, xylose, glucose, mannose, galactose, fucose and rhamnose; the fraction consisting essentially of the fraction having a molecular weight of 10,000 to 100,000 daltons and a sugar composition comprised of arabinose, xylose, glucose, mannose and galactose.

6. A method according to claim 5 wherein said fraction is applied in the form of a preparation suited for topical application to skin or mucosa portions of the human body.

7. A method according to claim 5 wherein said fraction is applied in the form of a preparation suited for topical application to the mouth, throat, nostril, eyelid, anus, rectum, urethra, vagina or an injured portion of the human body.

8. A method according to claim 5 wherein said fraction is applied in the form of a suppository, jelly, cream, cataplasma, ointment, plaster, inunction, liquid, spray, aerosol or external powder.

9. A method according to claim 5 wherein said fraction is applied in the form of a preparation for external application and contains said fraction in an amount of 0.1 to 5 weight %.

10. A method according to claim 5 wherein said fraction is applied in the form of a preparation for oral administration and each dosage unit contains said fraction in an amount of 10 to 10,000 mg.

11. A method according to claim 5 wherein said fraction is applied in the form of a preparation suited for parenteral administration.

12. A method according to claim 5 wherein said fraction is applied in the form of an injection containing 1 to 1,000 mg per dose of said fraction.

* * * * *

UNITED STATES PATENT AND TRADEMARK OFFICE
CERTIFICATE OF CORRECTION

PATENT NO.  : 5,283,239
DATED       : February 1, 1994
INVENTOR(S) : Junichi Koga, et al It is certified that error appears in the above-identified patent and that said Letters Patent is hereby corrected as shown below:

On the title page, item [54] and column 1, line 1, change "ABSORPTION" to --ADSORPTION--.

Column 7, line 3, change "absorption" to --adsorption--.

Signed and Sealed this

Twenty-fourth Day of November, 1998

Attest:

BRUCE LEHMAN

*Attesting Officer*  *Commissioner of Patents and Trademarks*